United States Patent
Levy et al.

(10) Patent No.: US 9,833,338 B2
(45) Date of Patent: Dec. 5, 2017

(54) TOOL FOR INTERVERTEBRAL CAGE

(71) Applicants: Mark M. Levy, Raanana (IL); Eran Ishay, Tel Aviv (IL); Jaffar Hleihil, Jish (IL); Assaf Guy, Allone Abba (IL)

(72) Inventors: Mark M. Levy, Raanana (IL); Eran Ishay, Tel Aviv (IL); Jaffar Hleihil, Jish (IL); Assaf Guy, Allone Abba (IL)

(73) Assignee: Expanding Orthopedics Inc., Memphis, TN (US)

( * ) Notice: Subject to any disclaimer, the term of this patent is extended or adjusted under 35 U.S.C. 154(b) by 20 days.

(21) Appl. No.: 14/754,727

(22) Filed: Jun. 30, 2015

(65) Prior Publication Data
US 2017/0000627 A1   Jan. 5, 2017

(51) Int. Cl.
 A61F 2/44    (2006.01)
 A61F 2/46    (2006.01)

(52) U.S. Cl.
 CPC .................. *A61F 2/4611* (2013.01)

(58) Field of Classification Search
 CPC .................................................. A61F 2/4611
 See application file for complete search history.

(56) References Cited

U.S. PATENT DOCUMENTS

| | | | |
|---|---|---|---|
| 6,395,007 B1 * | 5/2002 | Bhatnagar | A61B 17/3472 606/86 R |
| 6,511,481 B2 * | 1/2003 | von Hoffmann | A61B 17/68 606/60 |
| 8,105,382 B2 * | 1/2012 | Olmos | A61F 2/447 623/17.15 |
| 8,157,845 B2 * | 4/2012 | Warnick | A61F 2/4455 606/279 |
| 8,317,866 B2 * | 11/2012 | Palmatier | A61F 2/4455 623/17.11 |
| 8,574,301 B2 * | 11/2013 | Curran | A61F 2/447 623/17.16 |
| 2005/0256525 A1 * | 11/2005 | Culbert | A61K 31/713 606/53 |
| 2006/0178746 A1 * | 8/2006 | Bartish | A61F 2/4425 623/17.13 |
| 2007/0093841 A1 * | 4/2007 | Hoogland | A61B 17/1617 606/80 |
| 2009/0149857 A1 * | 6/2009 | Culbert | C07H 21/00 606/80 |
| 2009/0299478 A1 * | 12/2009 | Carls | A61F 2/4425 623/17.16 |
| 2010/0114147 A1 * | 5/2010 | Biyani | A61B 1/32 606/191 |
| 2011/0071527 A1 * | 3/2011 | Nelson | A61B 17/1624 606/85 |
| 2011/0144687 A1 * | 6/2011 | Kleiner | A61B 1/3135 606/192 |
| 2011/0230965 A1 * | 9/2011 | Schell | A61F 2/447 623/17.11 |

(Continued)

*Primary Examiner* — Ellen C Hammond
*Assistant Examiner* — Stuart S Bray
(74) *Attorney, Agent, or Firm* — Dekel Patent Ltd.; David Klein

(57) ABSTRACT

A tool assembly includes at least one tube and a slider disposed on a distal portion of the at least one tube. The slider includes a distal limiter movable between an extended position, in which the limiter protrudes distally from the slider, and a contracted position, in which the limiter does not protrude distally from the slider.

10 Claims, 8 Drawing Sheets

(56) References Cited

U.S. PATENT DOCUMENTS

| | | | |
|---|---|---|---|
| 2012/0232552 A1* | 9/2012 | Morgenstern Lopez | A61B 18/1487 606/45 |
| 2012/0232658 A1* | 9/2012 | Morgenstern Lopez | A61B 17/1757 623/17.16 |
| 2014/0155695 A1* | 6/2014 | Jansen | A61B 1/005 600/114 |
| 2014/0257296 A1* | 9/2014 | Morgenstern Lopez | A61B 17/1671 606/80 |
| 2014/0257490 A1* | 9/2014 | Himmelberger | A61F 2/44 623/17.16 |
| 2014/0277204 A1* | 9/2014 | Sandhu | A61F 2/4611 606/86 A |
| 2015/0073418 A1* | 3/2015 | Landes | A61B 17/1617 606/84 |
| 2015/0173917 A1* | 6/2015 | Radcliffe | A61F 2/4455 623/17.16 |
| 2016/0367265 A1* | 12/2016 | Morgenstern Lopez | A61B 17/1671 |

* cited by examiner

TOOL FOR INTERVERTEBRAL CAGE

FIELD OF THE INVENTION

The present invention relates generally to spinal implant devices, and particularly to tools for installing intervertebral cages for treatment of the spine.

BACKGROUND OF THE INVENTION

Intervertebral cages for spinal fusion help maintain disc space height, assist in the anterior column support of the spine, facilitate the fusion process due to the ability to hold bone graft in place and contribute to the overall alignment of the spine.

Several types of cages are used today through different surgical approaches. Several known techniques are used for fusion of the thoracic and lumbar spine. For example, cages for posterior or lateral approach are basically fixed spacers made out of titanium alloys or PEEK (polyether ether ketone) with chambers for bone graft location. They are usually rectangular in shape to be positioned in the disc space after discectomy. Regardless of the surgical technique, the intervertebral cage must be located inside the disc space in contact with the end plates preferably near the apophysial ring. Expandable cages are also known.

SUMMARY OF THE INVENTION

The present invention seeks to provide tools for installing intervertebral cages in the spine, as is described more in detail hereinbelow. The tools are useful for intervertebral fusion cage implanted through a posterior, trans-foraminal or lateral approach in open or minimally invasive surgery, with or without angular or parallel expansion. The tools are not limited to these kinds of intervertebral fusion cages and can be used with other cages and spinal devices.

The invention is applicable for many techniques, such as but not limited to, PLIF (posterior lumbar interbody fusion) through a posterior incision; TLIF (transforaminal lumbar interbody fusion), in which the approach is more from the side of the spinal canal through a midline incision or two smaller incisions at both sides of the midline; ALIF (anterior lumbar interbody fusion), through an anterior incision, such as in the lower abdominal area or on the side; and the Lateral Approach, a minimally invasive approach in which the disk space is accessed by means of retractors through a very small incision on the patient's side.

The invention provides a single tool (also called instrument) with an easy two-step procedure for insertion and expansion of implants. The tool may be used to control the articulation positioning of the implant, so that the insertion procedure is carried out in a controlled and secure manner. The same instrument may be used for insertion and removal of implants including non-expandable ones.

The instrument can be attached to the cage or any other implant and used for insertion in the disc space, inside vertebral bodies or any other bone with complete control of the device for ideal position without having to remove the instrument in the middle of the procedure.

The instrument and cages can be made from medical grade metals or polymers, or any other material, natural, synthetic or combined, and can be reusable or disposable.

The tool can be used for insertion and positioning of one or more segmented cages (with hinges for articulation) without expansion features, such as but not limited to, cages with two or more segments, cages with a central hinge, an eccentric hinge, a flexure, a free hinge or a lockable hinge (e.g., with a ratchet-like system), detent-type stoppers, screw holes at different radial locations for screw locking or simple friction of a locking pin and many others.

The tool can be used for insertion and positioning of articulated trial implants and non-expandable cages with or without the aid of imaging systems. In addition, expandable articulated cages can be inserted, positioned and expanded with the instrument. At the beginning of the procedure, the tool is attached to the cage and a distal limiter is used to limit articulation of the cage segments, so that it is easier to insert the cage into the patient. During insertion, the articulation is controlled by the distal limiter. The distal limiter can be connected to the implant so as to actively steer the implant. After verification of the proper position, the tool is detached and removed and the insertion procedure is finished. In the case of trial implants, position verification is followed by removal of the trial without detachment of the tool from the implant and the procedure continues with the insertion and positioning of the final implant. With expandable cages, verification of appropriate positioning is followed by the expansion of the cage with the expander screwdriver. After expansion and verification of the correct implant height, the tool is detached to finish the procedure.

There is thus provided in accordance with an embodiment of the present invention a tool assembly including at least one tube (such as an inner tube disposed in an outer tube), and a slider disposed on a distal portion of the at least one tube, the slider including a distal limiter movable between an extended position, in which the limiter protrudes distally from the slider, and a contracted position, in which the limiter does not protrude distally from the slider.

The tool assembly may further include an implant attached to the slider, the implant including segments movable with one another, wherein in the extended position, the limiter prevents movement of the segments with one another, and in the contracted position, the limiter permits movement of the segments with one another.

The at least one tube may include an implant holder knob at a proximal end thereof operative to grasp an implant.

The slider may include a proximal implant lock knob operative to move the limiter between the extended and contracted positions.

The inner tube may include a mark visible through an opening formed in the outer tube.

The tool assembly may further include an impact element movable on the at least one tube.

The tool assembly may further include an expander inserted in the tool and operative to mate with an expanding element of an implant.

The tool assembly may further include a safety mechanism operative to limit expansive movement of the expander.

The distal limiter may include an attachment element for reversibly attaching the distal limiter to a segment of an implant.

In another embodiment, the tool assembly includes only an inner and an outer tube, wherein the inner tube is operative to lock articulation of the cage for its proper insertion and positioning.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1A:
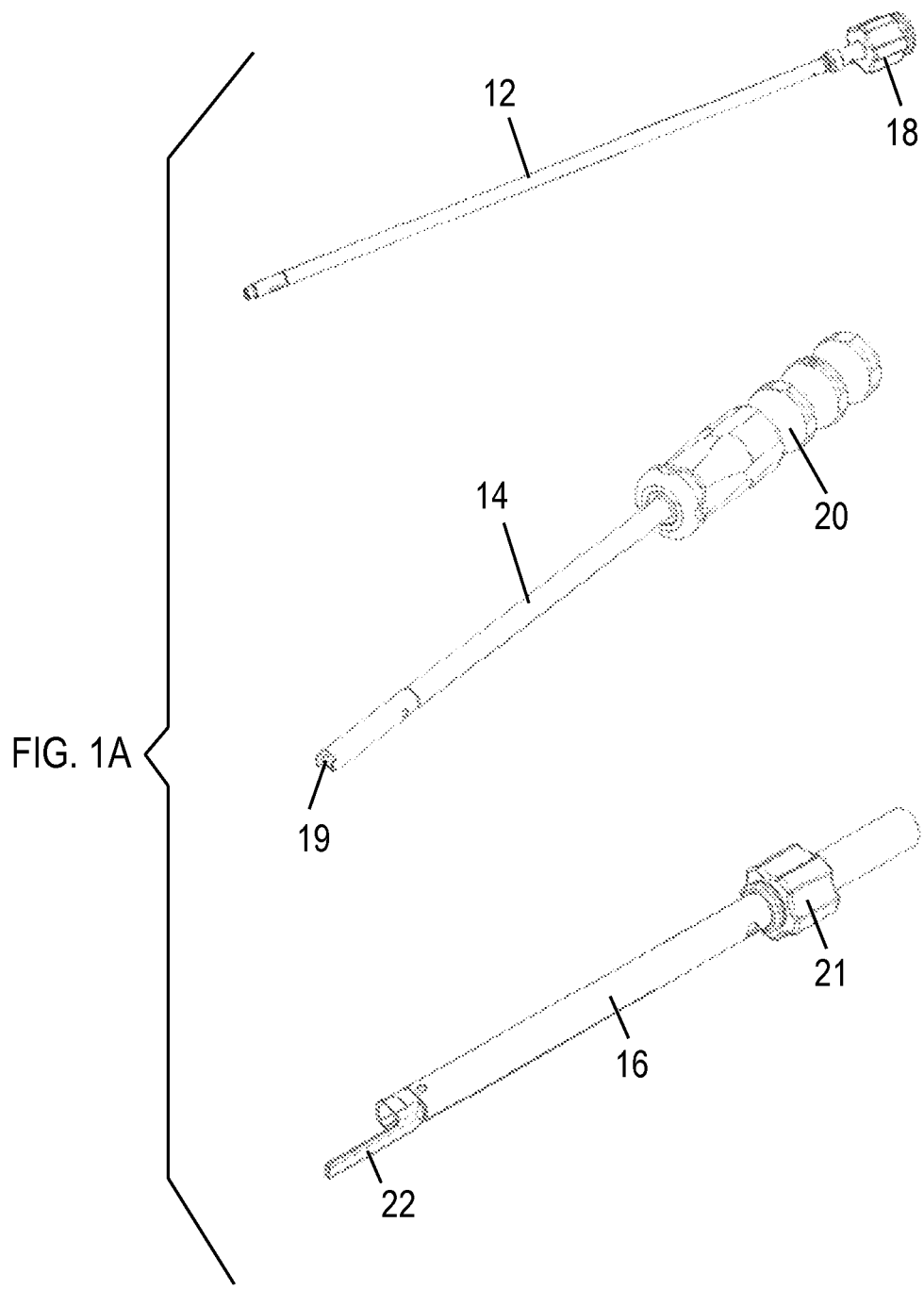
FIGS. 1A, 1B and 1C are perspective simplified illustrations of a tool for insertion, manipulation and removal of an intervertebral cage, constructed and operative in accordance with a non-limiting embodiment of the invention, wherein in FIG. 1A the parts of the tool are before assembly, in FIG. 1B the tool is assembled and a distal limiter is in an extended position and in FIG. 1C the limiter is in a contracted position.
Figure 1B:
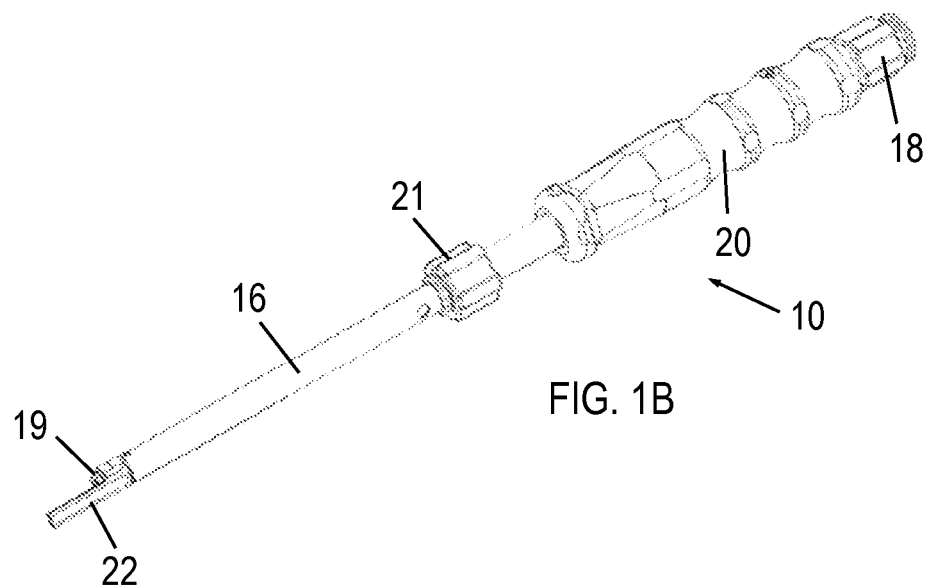
Figure 1C:
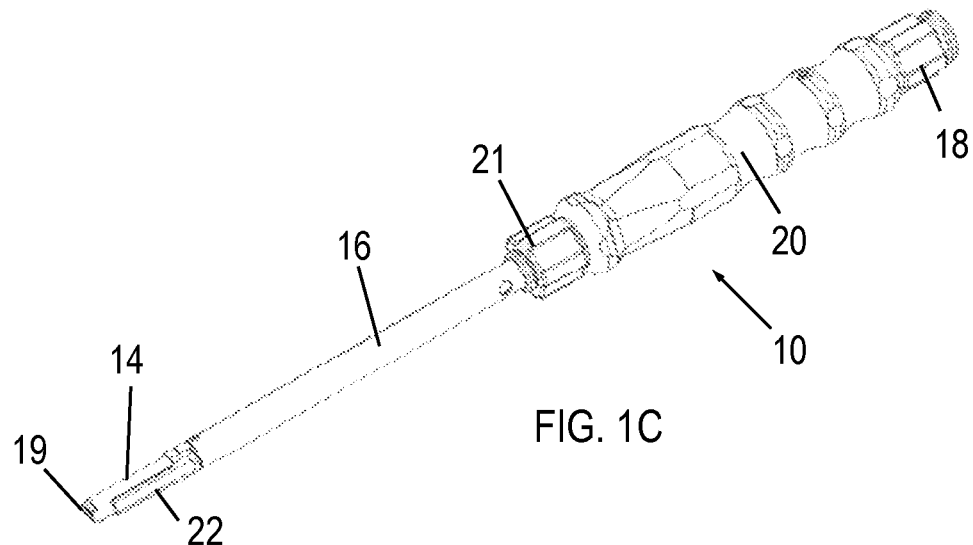

Reference is now made to FIGS. 1A-1C, which illustrate a tool 10 for use with intervertebral cages, constructed and operative in accordance with a non-limiting embodiment of the present invention.

Tool 10 includes at least one tube, which in the non-limiting illustrated embodiment includes an inner tube 12 and an outer tube 14, and a slider 16. The inner tube 12 has an implant holder knob 18 at a proximal end thereof (although alternatively knob 18 could be on the outer tube). The outer tube 14 has a handle 20 at a proximal end thereof. The outer tube 14 has a distal end with an implant interface member 19, configured to attach to an implant (for example, the member 19 may be a male member that can be secured to a female member of the implant). Alternatively interface member 19 could be on the inner tube.

Slider 16 has a proximal implant lock knob 21 and a distal limiter (e.g., tongue) 22 movable between an extended (locked) position (FIG. 1B), in which limiter 22 protrudes distally from slider 16, and a contracted (unlocked) position (FIG. 1C), in which limiter 22 does not protrude distally from slider 16. As will be explained below, in the extended position, limiter 22 is positioned next to two adjacent intervertebral cage segments so that the cage segments are blocked and prevented from pivoting with respect to each other, and in the contracted position, limiter 22 permits the cage segments to pivot with respect to each other.

Figure 2A:
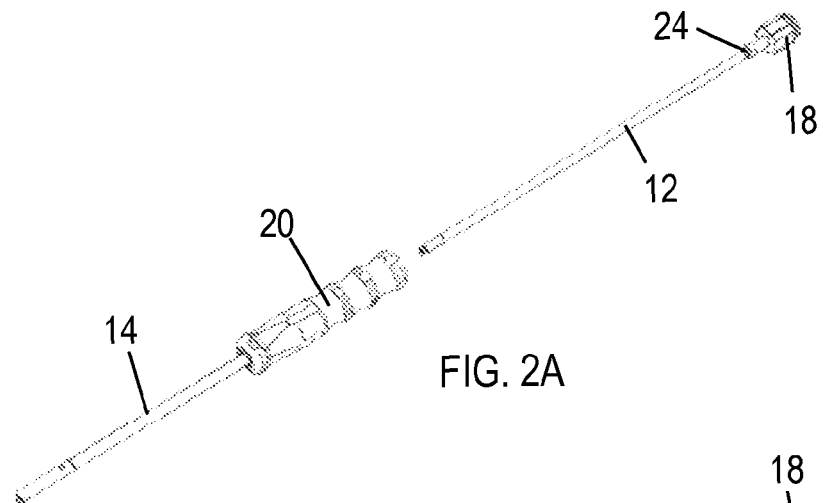
FIGS. 2A-2C are simplified illustrations of assembly of the tool, in accordance with a non-limiting embodiment of the invention.
Figure 2B:
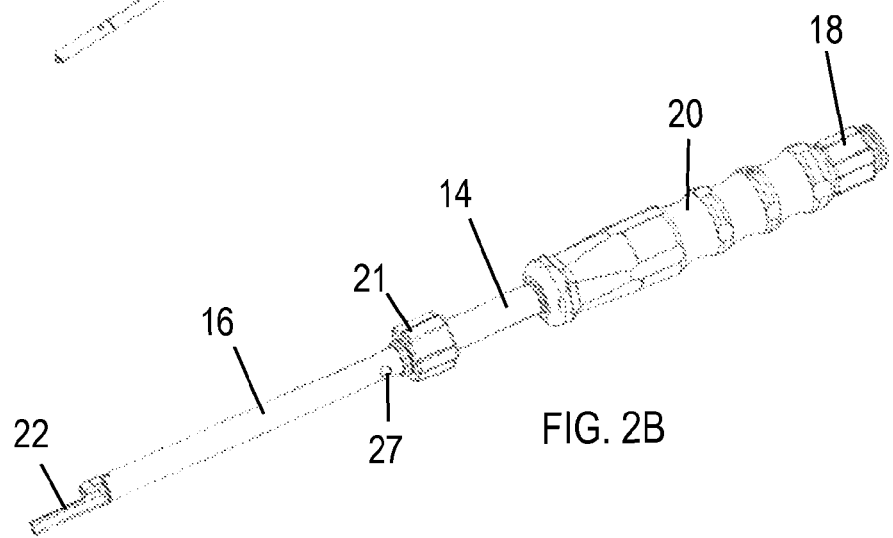
Figure 2C:
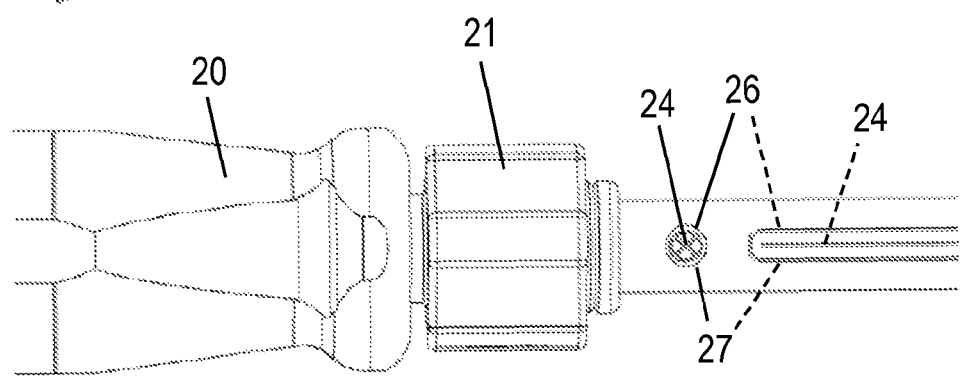

Reference is now made to FIGS. 2A-2C, which illustrate assembly of tool 10.

In FIG. 2A, inner tube 12 is inserted in outer tube 14 and attached thereto by turning the implant holder knob 18 (e.g., clockwise).

In FIG. 2B, slider 16 is inserted onto the distal portion of outer tube 14. Distal limiter 22 is correctly aligned by viewing a mark 24 on inner tube 12 through an opening (window) 26 in outer tube 14 and additionally or alternatively an opening (window) 27 in slider 16 (FIG. 2C). The mark 24 may be one color and/or shape to indicate to tool 10 is in the unlocked position (e.g., black and/or cross) and another color and/or shape to indicate to tool 10 is in the locked position (e.g., white and/or diamond). The openings 26 and 27 may be small, circular openings; additionally or alternatively, the openings 26 and 27 may be elongate as indicated by the broken line in FIG. 2C. The implant lock knob 21 is moved longitudinally until it stops and then lock knob 21 is rotated to the end (e.g., counterclockwise). It is noted that the invention can also be carried out with just one tube, such as the inner tube, in which case the slider is disposed on the inner tube.

For disassembly, implant lock knob 21 is rotated in the opposite direction (e.g., clockwise) until it is free to move and release slider 16. The implant holder knob 18 is pulled back (proximally) and turned (e.g., counterclockwise) to release inner tube 12 from outer tube 14.

Figure 3A:
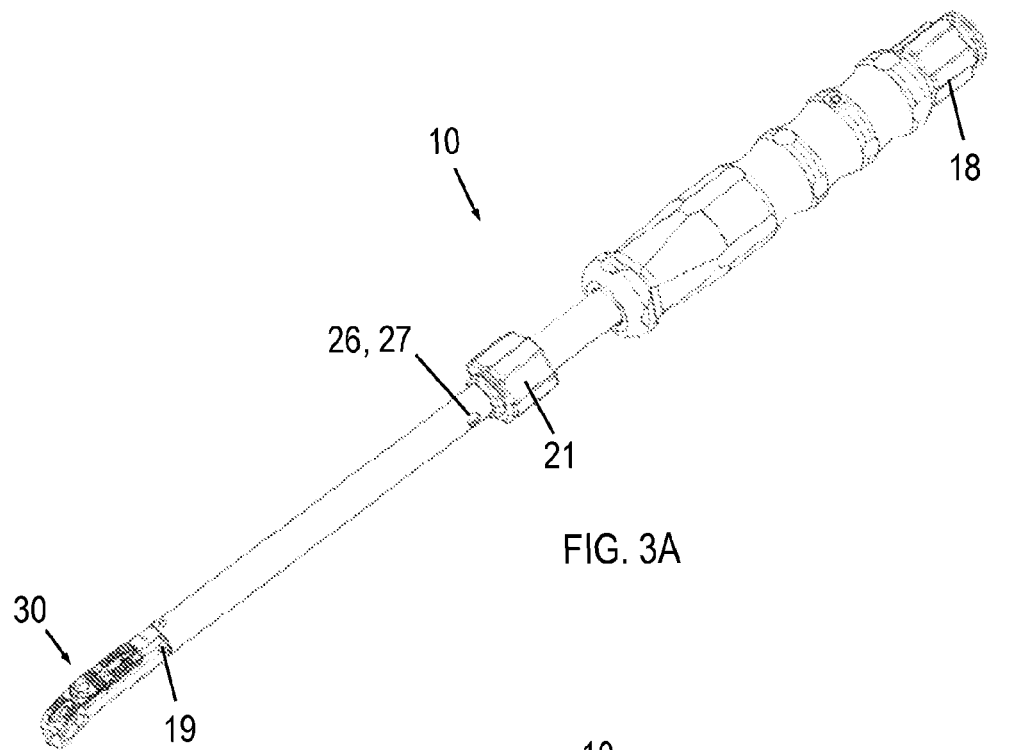
FIGS. 3A-3B are simplified illustrations of attachment of cage segments (implant) to the tool, in accordance with a non-limiting embodiment of the invention.
Figure 3B:
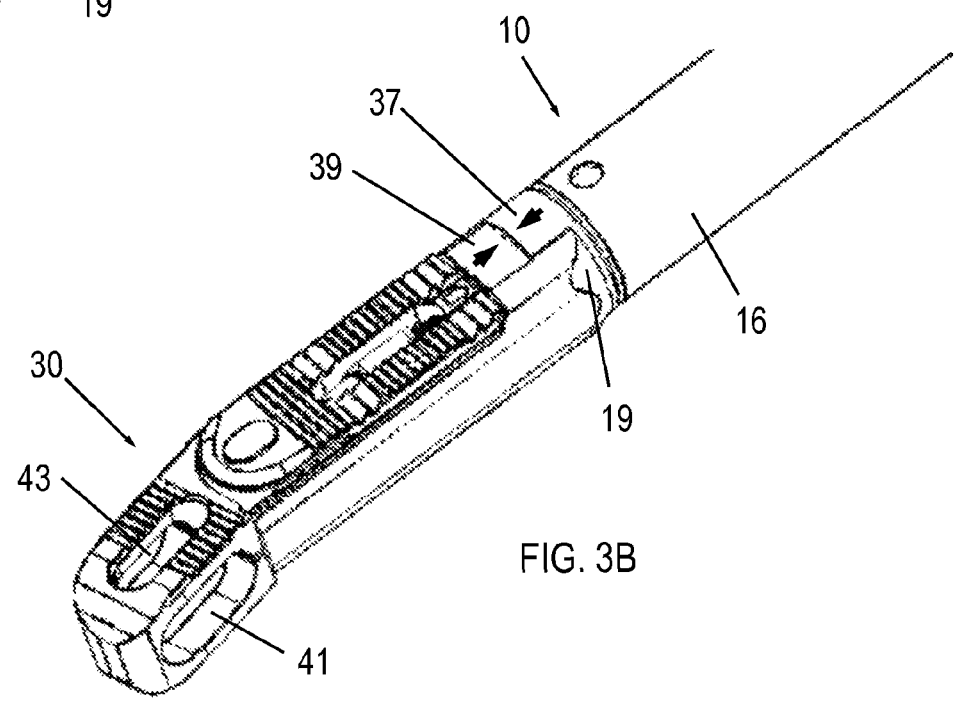

Reference is now made to FIGS. 3A-3B, which illustrate attachment of cage segments (implant) 30 to tool 10.

Initially, tool 10 is in the unlocked position as discussed above for FIGS. 2A-2C. The unlock mark appears in the outer tube window 26. An appropriate size cage is selected, such as by measuring the disc space height.

In FIG. 3A, cage segments 30 are attached to tool 10 by turning implant holder knob 18 (e.g., clockwise) until it stops, which attaches implant interface member 19 to the implant 30.

Implant lock knob 21 is turned (e.g., clockwise) and pushed forward until slider 16 stops against the segment 30. The lock mark appears in the window 26 and/or 27. When slider 16 contacts the segment 30, the first segment 30 cannot pivot with respect to the adjacent segment (FIG. 3A).

In FIG. 3B, an arrow 37 (or other marking) on the end of the tool 10 aligns with a corresponding marker 39 on the implant 30. There is no gap between the contact surfaces of the implant 30 and slider 16.

Figures 4A, 4B:
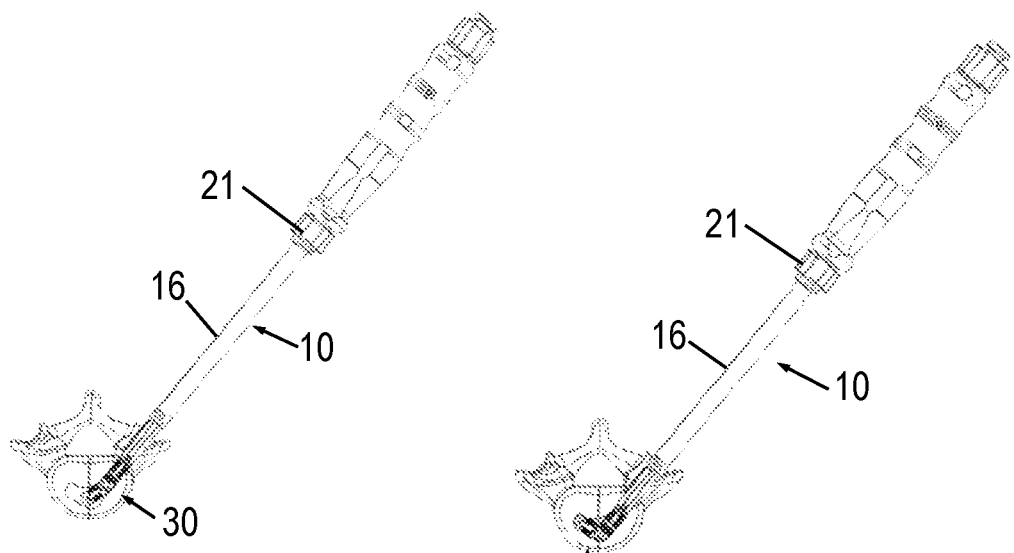
FIGS. 4A-4B are simplified illustrations of insertion and positioning cage segments (implant) in the disc space, in accordance with a non-limiting embodiment of the invention.

Reference is now made to FIGS. 4A-4B, which illustrate insertion (4A) and positioning (4B) of cage segments (implant) 30 in the disc space. FIG. 4A shows the implant 30 assembled on tool 10 and initially entering the curved disc space.

The correct orientation of implant 30 may be verified by a line mark on the outer tube 14 facing the sagittal plane. The implant tip should be orientated medially. It is preferable to maintain a 10-45° inclination between tool 10 and the sagittal plane during insertion of the implant.

Controlled and light hammering on tool 10 may be required to advance implant 30 into the intervertebral disc space. Imaging, such as fluoroscopy, may be used to confirm the position and fit of implant 30. The lateral view is normally sufficient using the tracking markers, but the anterior-posterior view may be used in case of doubt on the optimal medial position.

Implant 30 should be inserted with its upper and lower surfaces parallel to the vertebrae endplates.

In FIG. 4B, implant 30 is fully inserted into the disc space and the implant 30 has curved to match the curve of the disc space. The ability of the cage segments to pivot with respect to each other is what enables implant 30 to match the curve of the disc space.

In order to permit the cage segments to pivot with respect to each other, the implant lock knob 21 is turned (e.g., clockwise) and pulled back proximally so that distal limiter 22 of slider 16 (as shown in FIG. 1C) does not engage the implant 30. The unlock mark appears in window 26 (FIG. 2B or 2C).

Before unlocking implant 30, one may confirm by fluoroscopy or other imaging that the articulation point of the implant 30 has passed beyond the annulus entry point. Implant lock knob 21 is turned counterclockwise until it stops to avoid deformation of implant 30 or the outer tube.

Controlled and light hammering on tool 10 may be required to pivot implant 30 into the final position. One can use fluoroscopy or other imaging during the pivoting procedure to confirm fit and position of implant 30. Each segment of implant 30 has a medial/lateral opening 41 and an anterior/posterior opening 43 for position control (FIG. 3B).

Figure 5:
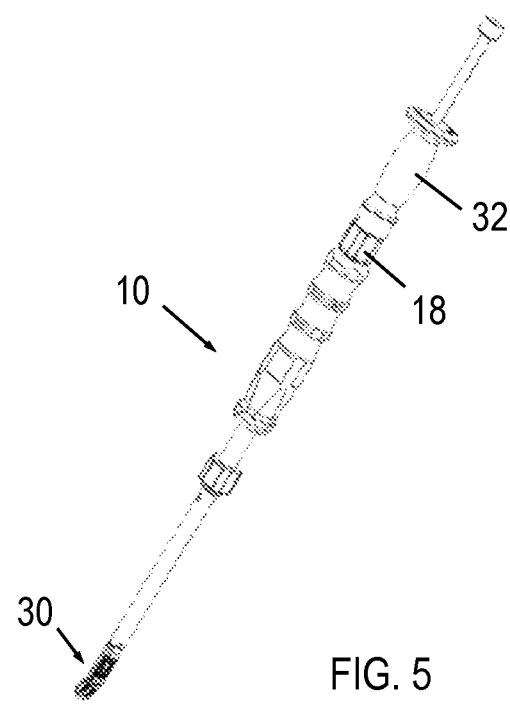
FIG. 5 is a simplified illustration of an impact element (hammer), which may be useful in removal of the implant from the disc space, in accordance with a non-limiting embodiment of the invention.

Reference is now made to FIG. 5. For removal of the implant from the disc space, an impact element (hammer) 32 may be slid onto the end of the implant holder knob 18. While holding the handle with one hand, an upward force to hammer 32 may be applied with the other hand. The hammering procedure may be repeated until the implant is removed. Hammer 32 may be removed from the handle by simply sliding hammer 32 out from the handle.

To detach the implant 30, the implant holder knob 18 may be turned (e.g., counterclockwise) until implant 30 is free.

Figure 6A:
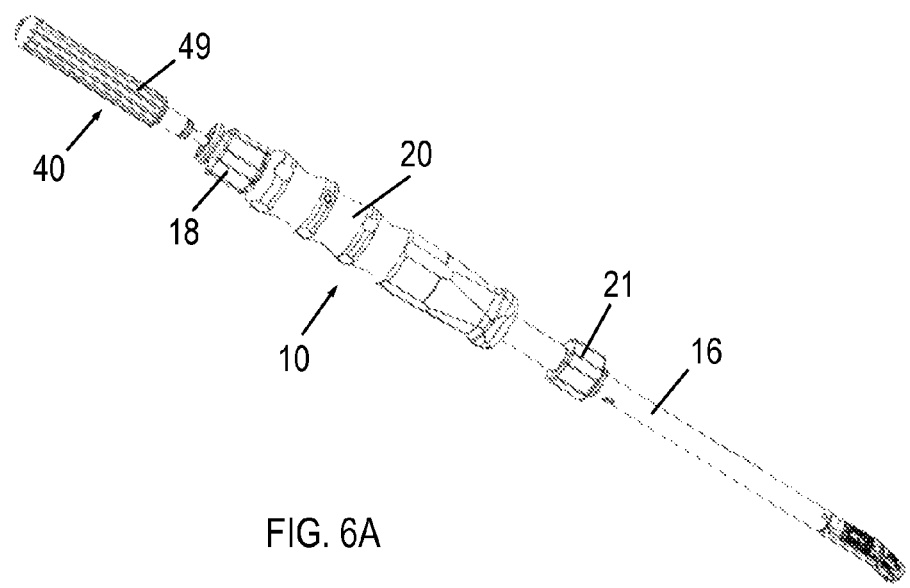
FIGS. 6A-6B are simplified illustrations of expansion of an expandable implant with the tool, in accordance with a non-limiting embodiment of the invention.
Figure 6B:
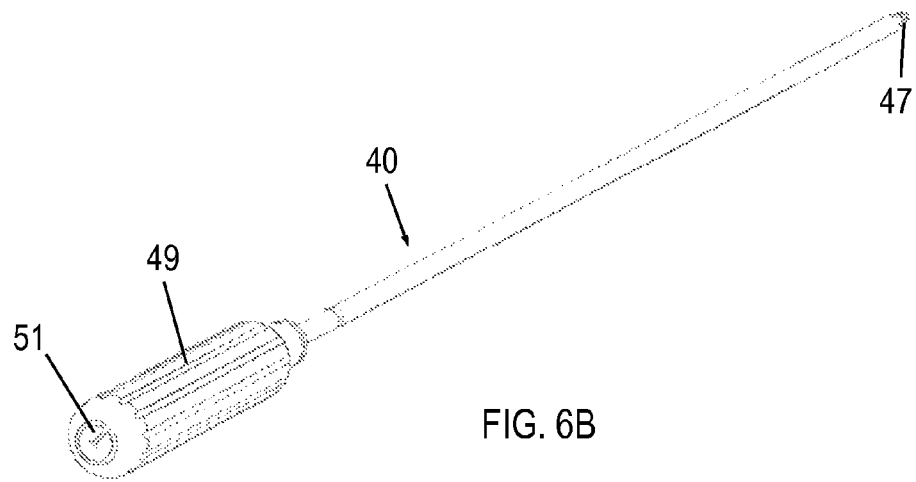

Reference is now made to FIGS. 6A-6B, which illustrate an expander 40, which may be used for the expansion of an expandable implant 30 with tool 10. After properly positioning implant 30 in the disc space, implant 30 is expanded by tightening expander 40.

FIG. 6A illustrates expander 40 fully inserted in tool 10. The expander 40 has a screwdriver end 47 (regular, TORX or other) to mate with the implant 30. The expander handle 49 is turned (e.g., clockwise) to expand the implant 30. Implant expansion adds height for lordosis correction. One or more marks 51 on the handle 49 (FIG. 6B) indicate the position of the handle 49 and may be used to keep track of the number of turns. After positioning and expansion, the inner tube can be used to introduce bone graft or bone substitutes to the implant inside the intervertebral disc space. In the case of a non-expandable cage, the bone graft is introduced through the inner tube after positioning.

Figure 7A:
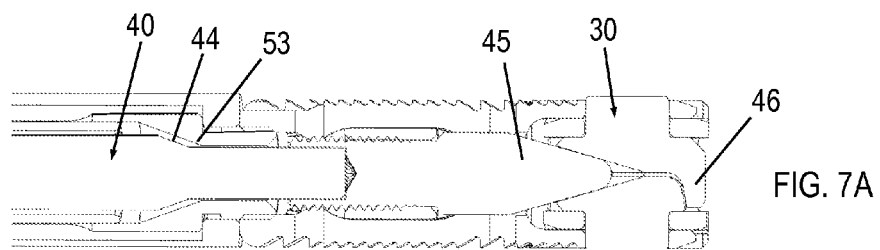
FIGS. 7A-7B are simplified illustrations of a safety feature that prevents overexpansion of the implant, in accordance with a non-limiting embodiment of the invention.
Figure 7B:
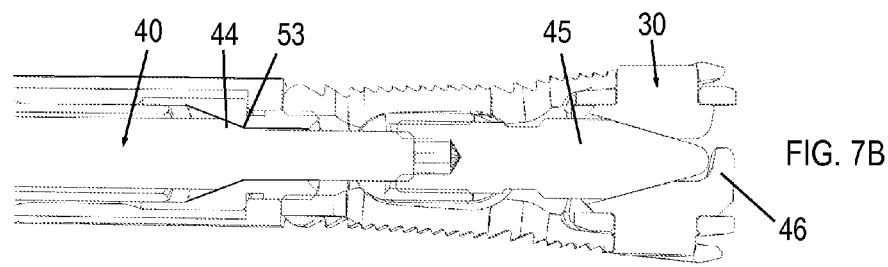

In one embodiment of the invention, there is a safety feature that prevents overexpansion of the implant, as illustrated in FIGS. 7A-7B.

The expander 40 may include a safety mechanism that limits the expansion of expandable cages up to a safe height. The safety mechanism may be a travel limiter 44, such as a shoulder formed at the end of expander 40 which abuts against an abutment 53 formed in the implant 30. Expander 40 expands implant 30 by turning a wedge screw 45 (or other fastener of the implant) in the implant. Advancement of the wedge screw 45 causes the outer contour of the implant to expand outwards as seen in FIG. 7B. As expander 40 is turned, it advances distally together with the wedge screw 45. As expander 40 is turned and advances distally, its distal advancement is blocked when travel limiter 44 abuts against abutment 53 (FIG. 7B). The abutment occurs upon achieving the maximum designed expansion (e.g., 2.8 mm or any other limit) (FIG. 7B), thereby preventing overexpansion of the implant. The safety mechanism may alternatively or additionally include an internal stopper 46 in the wedge mechanism of the expandable implant.

In addition, the expander handle (FIGS. 6A-6B) may be purposely made of a small size, which limits the amount of torque which can be applied to avoid over-torqueing. In other embodiments, the expander handle can be made in a T-shape or with a wider diameter.

Figure 8A:
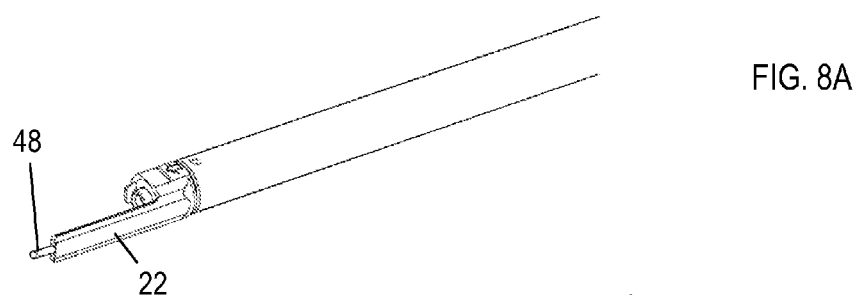
FIGS. 8A-8B are simplified illustrations of further features of the distal limiter, in accordance with other non-limiting embodiments of the invention, in which there is articulation control of the implant during insertion.
Figure 8B:

Reference is now made to FIGS. 8A-8B, which illustrate further features of the distal limiter 22, in accordance with other embodiments of the invention. In this embodiment, there is articulation control of the implant during insertion.

To allow a better control of cage segment steering during insertion, the distal limiter 22 may include an attachment element 48, such as a screw or any other connection, which will reversibly attach the limiter 22 to the distal segment of the implant. The implant is provided with a mating member for attachment element 48. Once limiter 22 is attached to the implant, the articulation movement of the implant can be controlled by the surgeon during insertion or removal. In some embodiments, the distal limiter 22 attachment is enhanced with a manually controlled ratchet-type button that can temporarily fix distal limiter 22 in a certain position for better handling of the instrument. When the desired position of the implant is achieved in the disc space at the required angle of articulation, the distal limiter 22 is then disconnected from the implant segment and the tool can be completely removed from the surgery site.

In other embodiments, the distal limiter 22 is made out of a hollow cylindrical shape (instead of a rectangular shape) or any other shape, including a supplementary screw-like or other attachment element 48.

Figure 9A:
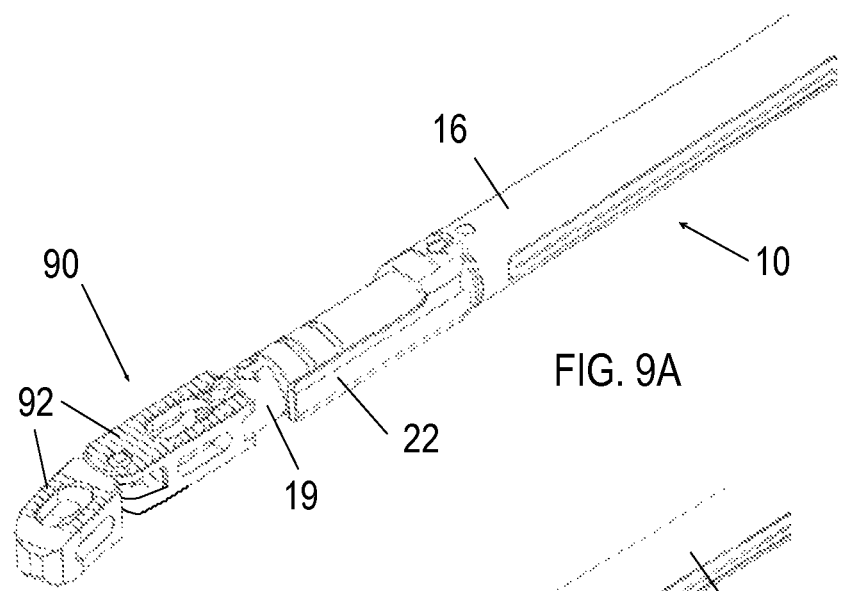
FIGS. 9A-9C are simplified illustrations of the tool, holding and positioning a non-expandable cage implant, in accordance with other non-limiting embodiments of the invention.
Figure 9B:
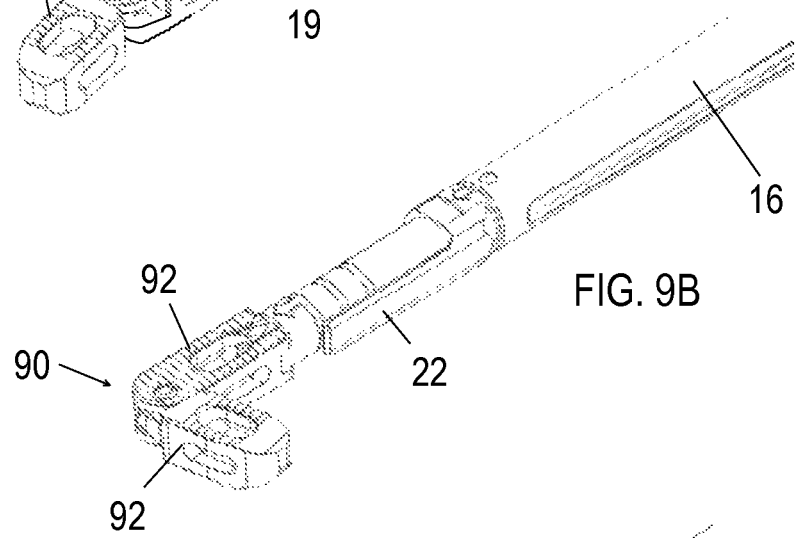
Figure 9C:
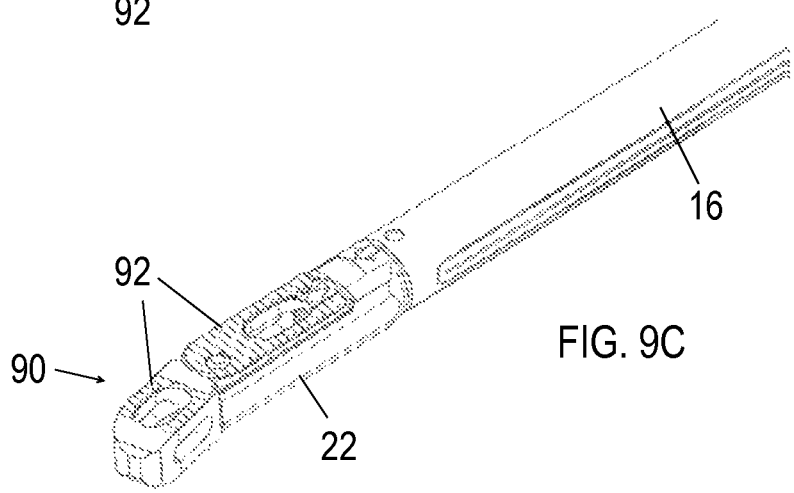

Reference is now made to FIGS. 9A-9C, which illustrate the tool 10, holding and positioning a non-expandable cage implant 90, in accordance with other non-limiting embodiments of the invention.

In FIG. 9A, cage segments 92 of implant 90 are attached to the implant interface member 19. The distal limiter 22 of slider 16 does not engage the segments 92 of implant 90.

In FIG. 9B, the cage segments 92 are free to move (e.g., pivot) with respect to each other. However, in FIG. 9C, distal limiter 22 of slider 16 engages segments 92, thereby preventing segments 92 from moving with respect to each other. The user can easily switch from one orientation to another to permit or block the pivoting of the segments.

What is claimed is:

1. A tool assembly comprising:
   at least one tube; and
   a slider, comprising a tubular element which is disposed on a distal portion of said at least one tube and which is slidable with respect to said at least one tube, said slider comprising a distal limiter movable between an extended position, in which said limiter protrudes distally from said at least one tube, and a contracted position, in which said limiter does not protrude distally from said at least one tube, said tubular element having an axial length, and said limiter comprising a tongue that extends further axially along said axial length and protrudes distally outwards from a distal end of said slider; and
   an implant attached to said slider, said implant comprising segments movable with one another by means of a joint between said segments, wherein in the extended position, said limiter prevents movement of said segments with one another by crossing over said joint, and in the contracted position, said limiter permits movement of said segments with one another.

2. The tool assembly according to claim 1, wherein said at least one tube comprises an inner tube disposed in an outer tube.

3. The tool assembly according to claim 2, wherein said inner tube comprises a mark visible through an opening formed in said outer tube.

4. The tool assembly according to claim 1, further comprising an impact element movable on said at least one tube.

5. The tool assembly according to claim 4, further comprising a safety mechanism operative to limit expansive movement of said expander.

6. The tool assembly according to claim 1, wherein said at least one tube comprises an implant holder knob at a proximal end thereof operative to grasp an implant.

7. The tool assembly according to claim 1, wherein said slider comprises a proximal implant lock knob operative to move said limiter between the extended and contracted positions.

8. The tool assembly according to claim 1, further comprising an expander inserted in said tool and operative to mate with an expanding element of an implant.

9. The tool assembly according to claim 1, wherein said distal limiter comprises an attachment element for reversibly attaching said distal limiter to a segment of an implant.

10. The tool assembly according to claim 1, further comprising bone graft or bone substitute introduced through said at least one tube.

\* \* \* \* \*